United States Patent
Flashinski et al.

(10) Patent No.: US 6,419,898 B1
(45) Date of Patent: Jul. 16, 2002

(54) INSECT COIL

(75) Inventors: Stanley J. Flashinski; Robert R. Emmrich; Anthony Sosa; David S. Eland, all of Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/661,350

(22) Filed: Sep. 14, 2000

(51) Int. Cl.$^7$ .............................................. A01N 25/18
(52) U.S. Cl. ........................... 424/40; 43/127; 424/406; 424/411; 424/417; 424/421; 424/DIG. 10; 428/906; 514/65; 514/521; 514/531; 514/919
(58) Field of Search ................................ 424/405, 409, 424/411, DIG. 10, 40, 406, 407, 417, 421; 514/919, 65, 531, 521; 43/127; 438/905

(56) References Cited

U.S. PATENT DOCUMENTS

| | | | |
|---|---|---|---|
| 3,796,002 A | 3/1974 | Katsuda | |
| 4,144,318 A | 3/1979 | D'Orazio | |
| 4,334,853 A | 6/1982 | Gardner | ........................ 431/2 |
| 4,515,768 A | 5/1985 | Hennart | |
| 4,605,549 A | 8/1986 | Carle | |
| D329,679 S | 9/1992 | Klapwald | |
| 5,447,713 A | 9/1995 | Eisner et al. | |
| 5,657,574 A | * 8/1997 | Kandathil et al. | ............ 43/125 |
| D385,942 S | 11/1997 | Kandathil | |
| 5,731,055 A | 3/1998 | Bernardo | |

FOREIGN PATENT DOCUMENTS

| | | |
|---|---|---|
| JP | 1-210488 | 8/1989 |
| WO | WO 98/42388 | 10/1998 |

OTHER PUBLICATIONS

Article: Mosquito Coils/Part III. Factors Influencing the Release of Pyrethrins form Coils by D. R. Maciver Research Laboratories, Pyrethrun Board of Kenya,/Fumakilla Coil Co., Japan(1963) Leaflet.
Article: the Effect of Binging Agents on the Mechanical and Physical Properties of Mosquito coils/J.M. Waithaka and J. H. Ombaka Odonde/Pyrethrum Baord of Kenya, P. O. Box 420, Nakuru, Kenya.
Article: Mosquito Coils/Part 1: General Description of Coils, Their Formulation and Manufacture/by D. R. Maciver/Research Laboratories, Pyrethrum Board of Kenya. Pyrethrins and Pyrethroids in Coils—A Review/R. Winney/ the Pyrethrum Bureau, Nakuru, Kenya.
Database WPI Section Ch, Week 199648 Derwent Publications Ltd., London, GB; Class C07, AN 1996–482053 XP002192225 & JP 08 245305 A (Fujimoto S), Sep. 24, 1996 abstract.
Database WPI Section PQ, Week 199924 Derwent Publications Ltd., London, GB; Class P14, AN 1999–280994 XP002192226 & JP 11 089507 A (Wakamatsu D), Apr. 6, 1999 abstract.
Database CA Online! Chemical Abstracts Service, Columbus, Ohio, US; retrieved form STN–Int'l, accession No. 91:169935 CA XP002192224 abstract & JP 54 076827 A (Dainippon Jochugiku) Jun. 19, 1979.
D.R. Maciver, "Mosquito Coils—Part I. General Description of Coils, their Formulation and Manufacture", Pyrethrum Post. 7, (2), pp. 22–27, (1963).
D.R. Maciver, "Mosquito Coils—Part III. Factors Influencing the Release of Pyrethrins from Coils", Pyrethrum Post. 7, (3), pp. 15–19, (1964).
R. Winney, "Pyrethrins and pyrethroids in coils—a review.", Pyrethrum Post. 13, (1), pp. 17–22, (1975).
J.M. Waithaka et al., "The Effect of Binding Agents on the Mechanical and Physical Properties of Mosquito Coils", Pyrethrum Post. 16, (2), pp. 35–42, (1986).
English Language Translation of Japansese Laid–Open Patent Publication No. 1–210488 (1989).

* cited by examiner

*Primary Examiner*—Neil Levy

(57) ABSTRACT

An insect coil having an extended, burnable body. The body has multiple treated zones bearing a volatilizable insect control active ingredient at insect controlling levels separated by spacing zones bearing a level of insect control active ingredient lesser than that of the treated zones. When burned, the insect coil releases bursts spaced in time of the active ingredient in insect controlling quantities. Preferably the spacing zones are active ingredient free, and the first treated zone to be burned has an active ingredient level higher than the remaining treated zones. A method of controlling insects by use of the insect coil also is disclosed.

9 Claims, 1 Drawing Sheet

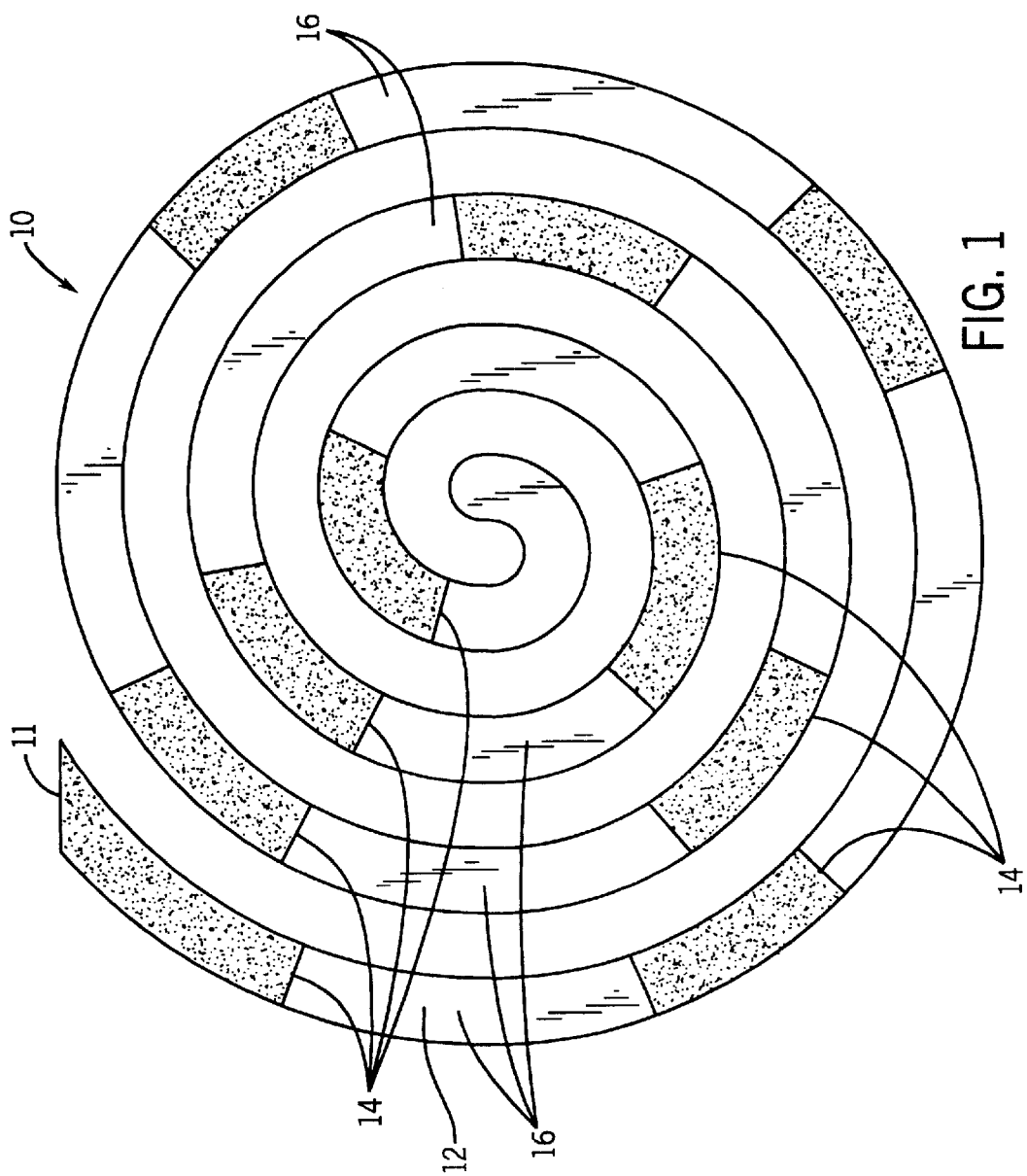

INSECT COIL

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The present invention relates to burnable coils for the control of insects. Insect coils for mosquito and other flying insect control are well known. Conventional coils are typically manufactured by preparing a dough made up of materials that, when dry and ignited, will slowly char, like punk. Conventional coils are treated with an insecticide, repellent, or other insect control active ingredient, most commonly by incorporating the active ingredient in the dough or by surface treating the dough. Coils are formed, usually as a strip of material cut or otherwise formed into a spiral shape, the strip having a substantially uniform cross section from the center of the coil to the outermost end.

D'Orazio, U.S. Pat. No. 4,144,318 is a typical example of such conventional coil technology. D'Orazio describes the formation of a strip of dough throughout which insecticide is uniformly mixed. The strip of dough is subsequently formed into the desired coil shape. Elsner et al., U.S. Pat. No. 5,447,713, describes the formation of a "board" of dough from which coil shapes are punched in much the way that a cookie cutter is used to cut cookies from a rolled-out layer of dough. Elsner et al. also describes surface treatment of either the "board" of dough or of the punched-out coil with a layer of insecticide uniformly and continuously applied with rollers. The disclosures of D'Orazio and Elsner et al. and of all other patents and publications subsequently referred to are incorporated herein by reference.

When the outermost end of a conventional coil is lit, the active ingredient in the as yet unburned portion of coil located immediately beside the burning end is heated and volatilizes. Conventional coils traditionally have been valued in part for their ability to deliver a continuous, linear discharge of volatile ingredient over a considerable length of time, typically three to eight hours or more.

In Kandathil et al., U.S. Pat. No. 5,657,574, however, an insect coil is disclosed wherein the strip of material of which the coil is formed has active ingredient uniformly distributed throughout the material but has a greater cross-sectional area near its outermost end. By this means, the coil is made to deliver active ingredient at a greater rate when it is first lit. This higher, initial dose of active ingredient is intended to quickly establish an effective, insect controlling level of active ingredient in the previously untreated air in the vicinity of the coil. The remainder of the coil shown in Kandathil is of the traditional, generally uniform cross section. Kandathil utilizes the traditional incorporation of active ingredient in the dough from which the coil is formed, causing a continuous release of active ingredient once the coil is lit and a substantially linear release rate after the enlarged initial end has burned.

It is known to provide for doses of perfume delivered to the air for air freshening. Various means for such perfume delivery are known, including, by way of example, by delivering periodic sprays of scent or by continuously moving a web containing separated deposits of volatilizable perfumes over a heater, with each deposit being released only as it approaches the heater. This is done because a human's ability to perceive scent fatigues if a perfume level is constant, causing a uniform scent level to become progressively less noticeable. In contrast, with periodic scent delivery systems, each new burst of scent is noticed and the effects of olfactory fatigue are lessened.

The insect control active ingredients in an insect coil account for a significant portion of the cost of making the coil. Furthermore, although the active ingredient level dispensed by present day insect coils can easily be both effective and safe to people and animals, in many users' minds still lower active ingredient levels are appealing, at least if insect control effectiveness is maintained. It can therefore be seen that there is a need for an improved insect coil and method for controlling insects that achieves either (1) insect control at a level comparable to that achievable with conventional coils while, at the same time, requiring only a reduced amount of insect control active ingredient or (2) a higher level of insect control without the need to use an increased amount of insect control active ingredient.

BRIEF SUMMARY OF THE INVENTION

Insect "control" is defined to mean killing insects or altering insect behavior. "Insect" is defined to include actual insects as well as arachnids and other small animals commonly controlled with insects. Altering insect behavior includes but is not limited to knocking insects down, repelling them, reducing their tendency to bite, altering reproduction or development, and the like. An "insect control active ingredient" is an ingredient that can be volatilized via an insect coil with insect controlling effects. Release of an insect control active ingredient by a burning insect coil shall be deemed "effective" and in an "effective insect controlling amount" if not less than 50 percent of caged *Aedes aegypti* mosquitoes are knocked down within 120 minutes upon exposure to the release of the insect control active ingredient in wind-free conditions within a closed, 20 cubic meter chamber. Insects are "knocked down" if they are incapacitated and rendered inactive, whether or not actually dead. An insect controlling level of an insect control active ingredient applied to a portion of an insect coil is that amount which causes a release of the insect control active ingredient in effective insect controlling amounts when that portion of the coil is burned.

The invention provides an insect coil having an extended, burnable body. The body may be straight or may be formed into any desired pattern, including but not limited to a spiral, rectangle, or oval. A spiral shape is preferred for its compactness and freedom from sharp turns, which can cause burning anomalies. The body has multiple treated zones each bearing a volatilizable insect control active ingredient in an amount sufficient to achieve insect controlling levels when released and combined with any insect control active ingredient previously released from the insect coil and still present within the area to be protected by the coil. "Multiple" is defined to mean at least two. The treated zones are separated from each other by spacing zones that bear a level of insect control active ingredient lesser than that of the treated zones. Consequently, when the insect coil is ignited and the treated zones burn in sequence, the insect coil releases bursts spaced in time of the active ingredient in insect controlling quantities. Preferably, the spacing zones are substantially free of the insect control active ingredient.

In a preferred embodiment, the insect coil of the invention has an ignition end, at which it is to be ignited, and the treated zone closest to the ignition end bears a level of insect control active ingredient greater than that of the remaining treated zones. As a consequence, the first treated zone to burn releases a first amount of the insect control active ingredient larger than amounts released by the subsequent treated zones. The surrounding atmosphere is free of the active ingredient when the first treated zone begins to burn. However, when subsequent treated zones are reached, the surrounding atmosphere may be expected to still contain a residual level of active ingredient from previously burned treated zones. Thus, while a greater initial amount of active ingredient is useful to quickly establish an effective insect controlling amount of active in the air, a lesser amount of active ingredient can be sufficient to merely maintain a pre-established, residual active ingredient concentration at effective levels.

Any insect control active ingredient that can be volatilized via an insect coil with insect controlling effects may be used in the coil of the invention. The art is aware of many such active ingredients. Preferred for reasons of cost and effectiveness are active ingredients selected from the group consisting of pyrethrum, pyrethroids, insect-repelling natural volatile oils, insect growth regulators, and mixtures thereof. The group consisting of pyrethrum, resmethrin, bioallethrin, allethrin, esbiothrin, and mixtures thereof is especially preferred. If desired, selected treated zones of the insect coil of the invention can be treated with an insect control active ingredient different from the insect control active ingredient with which other selected treated zones are treated.

The method of the invention for controlling insects includes the following steps. First, an insect coil is provided having an extended, burnable body. The body has an ignition end and multiple treated zones. Each treated zone bears a volatilizable insect control active ingredient in a quantity that is sufficient to be an effective insect controlling amount of insect control active ingredient when combined with any such active ingredient remaining from a previous release of active ingredient from the insect coil. The treated zones are separated by spacing zones bearing a level of insect control active ingredient lesser than that of the treated zones. The burnable body is placed in the vicinity of insects to be controlled, and the ignition end of the burnable body is ignited. The burnable body is allowed to burn from the ignition end to release bursts spaced in time of the active ingredient in insect controlling quantities. Preferably, the spacing zones are substantially free of the insect control active ingredient. It is even more preferred that the treated zone closest to the ignition end bear a level of insect control active ingredient greater than that of the remaining treated zones.

BRIEF DESCRIPTION OF THE DRAWINGS

FIG. 1 is a plan view of an insect coil of the invention, from above, with treated zones indicated with shading.

DETAILED DESCRIPTION OF THE INVENTION

Turning now to the drawing, an insect coil of a preferred, coiled spiral shape is shown generally at 10. The insect coil 10 has an ignition end 11 and an extended, burnable body 12. The body 12 has multiple treated zones 14 (shown schematically as shaded areas, although no visual difference in fact is required). The treated zones 14 are separated from each other by spacing zones 16 (shown schematically as unshaded areas).

Each treated zone 14 bears a volatilizable insect control active ingredient in an amount sufficient to achieve insect controlling levels when released and combined with any insect control active ingredient previously released from the insect coil 10 and still present in the area within which insects are to be controlled. The spacing zones 16 bear a level of insect control active ingredient lesser than that of the treated zones 14. When the insect coil 10 is ignited at the ignition end 11, a charring line of fire burns along the coil, consuming it and releasing insect control active ingredient from the heated portion of the coil adjacent to the line of fire.

Because of the spaced locations of the treated zones 14, insect control active ingredient is released in bursts, spaced in time, as the line of fire reaches successive treated zones. The locations and widths of the treated and spacing zones 14,16 and the rate of burn of the insect coil 10 determine the timing of the bursts of released insect control active ingredient.

In the preferred embodiment of the insect coil 10 of the invention, the coil is made of a conventional, predominantly cellulosic dough by conventional methods. Preferably, the dough is formed into a moist sheet, and insect coils are cut from it by use of a cutter device resembling a cookie cutter. To avoid waste, insect coils are conventionally and preferably cut as inter-leaved, double coils that are separated into single coils either by an end user or in the manufacturing process. The cut coils are dried.

The insect coils 10 are treated with insect control active ingredient either before or (preferably) after drying, and preferably the active ingredient is deposited preferentially on or immediately near the surface of the coil. Esbiothrin is the preferred active ingredient and is applied to the coil dissolved in a convenient, conventional solvent. Ethanol or any suitable, conventional volatile solvent can be used. Preferably the esbiothrin solution is applied to the coil by spraying from a multi-orifice spray head that directs the active ingredient preferentially to the treated zones 14. In an insect coil 10 treated by this method, the spacing zones 16 commonly receive some active ingredient as overspray. Nevertheless, the spacing zones 16 have a concentration of active ingredient that is less than that of the treated zones 14.

If a more controlled demarcation between treated and spacing zones 14,16 is desired, active ingredient can be applied to the insect coil 10 by pad, roller, screen, flexographic, ink jet-style, or other conventional printing techniques. Alternatively, and as a second, preferred method of manufacture, a stencil can be located over the insect coil 10, to cover the spacing zones 16, leaving the treated zones 14 exposed to a sprayed application of active ingredient.

Typically, a conventional insect coil designed to burn for approximately six hours is treated with approximately 12 mg of esbiothrin uniformly distributed along the length of the coil. A preferred insect coil 10 of the invention is treated with the same overall amount of esbiothrin but now with the esbiothrin applied to treated zones 14 at the rate of approximately 1.0 mg per treated zone, with the treated zones being approximately 30 to 35 minutes apart in burn time. Such an insect coil 10 exhibits superior insect control when compared to the conventional coil bearing the same amount of insect control active ingredient.

Even more superior results can be obtained by treating a treated zone 14 located near the ignition end 11 of the insect coil 10 with an extra amount of insect control active ingredient. This causes an initial, heavier burst of active ingredient to be dispensed when the insect coil 10 is first lighted. This tends to clear insects from the space to be protected and to provide a residual dose of active ingredient to combine with the doses dispensed from successive treated zones.

The preceding description is merely of preferred embodiments of the invention. One skilled in the art will readily apprehend alternative embodiments that nevertheless fall within the scope and breadth of the invention. Thus, the claims should be looked to in order to understand the full scope of the invention.

INDUSTRIAL APPLICABILITY

An insect coil and a method of controlling insects is provided for the practical control of mosquitoes and other noxious insects.

What is claimed is:

1. An insect coil having an extended, burnable body, the body having multiple treated zones each bearing a volatilizable insect control active ingredient in an amount sufficient to achieve insect controlling levels when released and combined with any insect control active ingredient previously released from the insect coil and still present in the area within which insects are to be controlled, the treated zones being separated from each other by spacing zones along the coil bearing a level of insect control active ingredient lesser than that of the treated zones to cause the insect coil, when burned, to release bursts spaced in time of the active ingredient in insect controlling quantities;

wherein the spacing zones are a part of the burnable body and the insect coil has a treated zone adjacent the ignition end with a first concentration of a specified insect control active ingredient deposited on its surface, and wherein a surface of a spacing zone adjacent said treated zone is either essentially free of that specified insect control active ingredient or has deposited thereon a lesser concentration of that ingredient than the first concentration.

2. The insect coil of claim 1 wherein the spacing zones are substantially free of the insect control active ingredient.

3. The insect coil of claim 1 wherein the insect coil has an ignition end at which it is to be ignited, and the treated zone closest to the ignition end bears a level of insect control active ingredient greater than that of the remaining treated zones.

4. The insect coil of claim 1 wherein the insect control active ingredient is selected from the group consisting of pyrethrum, pyrethroids, insect-repelling natural volatile oils, insect growth regulators, and mixtures thereof.

5. The insect coil of claim 1 wherein the insect control active ingredient is selected from the group consisting of pyrethrum, resmethrin, bioallethrin, allethrin, esbiothrin, and mixtures thereof.

6. The insect coil of claim 1 wherein selected treated zones are treated with an insect control active ingredient different from the insect control active ingredient with which other selected treated zones are treated.

7. A method of controlling insects comprising the steps of:
a. providing an insect coil having an extended, burnable body, the body having an ignition end and multiple treated zones each bearing a volatilizable insect control active ingredient in an amount sufficient to achieve insect controlling levels when released and combined with any insect control active ingredient previously released from the insect coil and still present in the area within which insects are to be controlled, the treated zones being separated by spacing zones along the coil bearing a level of insect control active ingredient lesser than that of the treated zones;

wherein the spacing zones are a part of the burnable body and the insect coil has a treated zone adjacent the ignition end with a first concentration of a specified insect control active ingredient deposited on its surface, and wherein a surface of a spacing zone adjacent said treated zone is either essentially free of that specified insect control active ingredient or has deposited thereon a lesser concentration of that ingredient than the first concentration;

b. igniting the ignition end of the burnable body; and
c. allowing the burnable body to burn from the ignition end in the vicinity of insects to be controlled to release bursts spaced in time of the active ingredient in insect controlling quantities.

8. The method of claim 7 wherein the spacing zones are substantially free of the insect control active ingredient.

9. The method of claim 7 wherein the treated zone closest to the ignition end bears a level of insect control active ingredient greater than that of the remaining treated zones.

* * * * *